United States Patent
Benner et al.

(10) Patent No.: US 12,023,683 B1
(45) Date of Patent: Jul. 2, 2024

(54) SYSTEM FOR PRODUCING SOLVENT FREE FULL SPECTRUM CANNIBIS EXTRACT

(71) Applicant: DELMARVA HEMP, LLC, Salisbury, MD (US)

(72) Inventors: Jeffrey David Benner, Salisbury, MD (US); David Benton McGiffin, Salisbury, MD (US); Larry Maurice Douglas, Parsonsburg, MD (US)

(73) Assignee: Delmarva Hemp, LLC, Salisbury, MD (US)

( * ) Notice: Subject to any disclaimer, the term of this patent is extended or adjusted under 35 U.S.C. 154(b) by 324 days.

(21) Appl. No.: 17/653,887

(22) Filed: Mar. 8, 2022

Related U.S. Application Data (62) Division of application No. 15/929,971, filed on Jun. 1, 2020, now Pat. No. 11,291,699.

(Continued)

(51) Int. Cl.
| | |
|---|---|
| *B02C 23/10* | (2006.01) |
| *B02C 19/18* | (2006.01) |
| *B02C 23/06* | (2006.01) |

(52) U.S. Cl.
CPC ............ *B02C 23/10* (2013.01); *B02C 19/186* (2013.01); *B02C 23/06* (2013.01);
(Continued)

(58) Field of Classification Search
CPC . B02C 19/186; B02C 2019/183; B02C 23/06; B02C 23/10; A61K 2236/15; A61K 2236/37
See application file for complete search history.

(56) References Cited

U.S. PATENT DOCUMENTS

| | | | |
|---|---|---|---|
| 8,716,537 B2 * | 5/2014 | Medoff ................. | B01J 19/085 |
| | | | 568/903 |
| 9,937,219 B2 | 4/2018 | Raderman | |

(Continued)

FOREIGN PATENT DOCUMENTS

| | | |
|---|---|---|
| CN | 107898826 A | 4/2018 |
| CN | 109574810 A | 4/2019 |

(Continued)

OTHER PUBLICATIONS

CBD Awareness Project: "CBD Extraction Methods: How CBD Oil Is Made." https://www.cbdoil.org/cbd-extraction-methods/ (published Mar. 30, 2019).

(Continued)

*Primary Examiner* — Faye Francis
(74) *Attorney, Agent, or Firm* — Rosenberg, Klein & Lee (57) ABSTRACT

A system for preparing a medicinal substance containing full spectrum of therapeutically desirable substances in naturally occurring proportions found in hemp plants, carried out by grinding a whole hemp plant to produce fine particles material, and exposing the fine particles material to an elevated pressure (11 PSI-15 PSI) and a reaction temperature maintained in a range of 230 F-250 F which is below a boiling point of the phyto-cannabinoids, terpenes and flavonoids, thus providing enhanced conditions for solvent-free extraction of the therapeutically desirable substances and diffusing the extracted substances into the carrier oil at an enhanced rate. Thus producing an infused oil final product containing a full spectrum phyto-cannabinoids, terpenes and flavonoids in naturally occurring proportions.

15 Claims, 1 Drawing Sheet

Related U.S. Application Data (60) Provisional application No. 62/947,925, filed on Dec. 13, 2019.

(52) U.S. Cl.
CPC ...... *A61K 2236/15* (2013.01); *A61K 2236/37* (2013.01); *B02C 2019/183* (2013.01)

(56) References Cited

U.S. PATENT DOCUMENTS

| | | | |
|---|---|---|---|
| 9,950,275 B1 | 4/2018 | Ruben et al. | |
| 10,011,804 B2 | 7/2018 | Mancosky | |
| 10,213,788 B2 * | 2/2019 | Bates | B02C 19/16 |
| 10,308,625 B1 | 6/2019 | Ruben et al. | |
| 2015/0126754 A1 | 5/2015 | Fernandez Cid et al. | |
| 2017/0202895 A1 * | 7/2017 | Hugh | A61K 31/05 |
| 2019/0192993 A1 | 6/2019 | Levy et al. | |
| 2019/0201809 A1 | 7/2019 | Nadal Roura | |
| 2019/0231833 A1 | 8/2019 | Garti et al. | |
| 2019/0276384 A1 | 9/2019 | Chen et al. | |
| 2020/0221644 A1 * | 7/2020 | Nahtigal | B02C 18/10 |
| 2021/0046525 A1 * | 2/2021 | Lee | C10L 5/44 |
| 2021/0114038 A1 * | 4/2021 | Sandnes | B02C 21/02 |
| 2023/0060109 A1 * | 2/2023 | Lee | C05F 5/00 |

FOREIGN PATENT DOCUMENTS

| | | | | |
|---|---|---|---|---|
| CN | 109809969 A | | 5/2019 | |
| CN | 110420697 A | * | 11/2019 | ............ B02C 13/02 |
| WO | 2016153347 A1 | | 9/2016 | |
| WO | 2018187500 A1 | | 10/2018 | |
| WO | 2019020738 A1 | | 1/2019 | |
| WO | 2019074614 A2 | | 4/2019 | |

OTHER PUBLICATIONS

Intrinsic Hemp: "How is CBD Extracted? Common CBD Extraction Methods." https://intrinsichemp.com/how-is-cbd-extracted/ (last updated Sep. 15, 2019).

Kishani et al. "Solubility of Softwood Hemicelluloses." Biomacromolecules 19(4) (Apr. 2018), pp. 1245-1255. doi: 10.1021/acs.biomac.8b00088.

Mohd et al. "Dissolution of cellulose in ionic liquid: a review." AIP Conf. Proc. 1809 (Feb. 2017), p. 020035. doi:10.1063/1.4975450.

Russo. "Taming THC: potential cannabis synergy and phytocannabinoid-terpenoid entourage effects." British J Pharm. 163 (Jan. 2011) pp. 1344-1364. doi:10.1111/j.1476-5381.2011.01238.

Sameni et al. "Solubility of Lignin and Acetylated Lignin in Organic Solvents." Bioresources 12(1) (Jan. 2017), pp. 1548-1565. doi:10.15376/biores.12.1.1548-65.

Thomsen et al. "Hemp raw materials: The effect of cultivar, growth conditions and pretreatment on the chemical composition of the fibres." Risø National Laboratory, Risø-R-1507 (Mar. 2005).

* cited by examiner

SYSTEM FOR PRODUCING SOLVENT FREE FULL SPECTRUM CANNIBIS EXTRACT

FIELD OF THE INVENTION

The present invention is directed to processing of *cannabis*/hemp plants for medicinal purposes, and particularly, to preparation of cannabinoids based therapeutically desired substances.

Even more in particular, the present invention is directed to a system for extracting a full spectrum of phyto-cannabinoids, terpenes and flavonoids from a whole *cannabis*/hemp plant for infusing them into a carrier oil using precisely controlled reaction pressure/temperature to prevent an inadvertent waste of the therapeutically desirable compounds of the plants due to vaporization at excessive reaction temperatures.

The present invention is also directed to a solvent-free extraction of the therapeutic compounds such as phyto-cannabinoids, terpenes and flavonoids, in their naturally occurring proportions, from *cannabis*/hemp plants into a carrier oil to produce a concentrated full spectrum infusion oil with the preserved synergy of the Entourage effect.

The present invention is further directed to a system for extracting and infusing cannabinoids in a carrier oil using enhanced pressure and temperature combinations which requires no solvents for the extraction/concentration process, thus directly producing a detoxified final product free of a residual solvent, thereby obviating the need for an additional post-extraction detoxification of the infused carrier oil.

The present invention is also directed to an enhanced oil extraction of *cannabis* and/or hemp plants which may be performed using inexpensive equipment which is flexible enough to process small batches and be scaled-up to handle large amounts of *cannabis*/hemp per day.

In addition, the present invention is directed to a system for extracting therapeutically desirable compounds from *cannabis*/hemp plant material and infusing into a carrier oil by performing multiple processing tasks in the same reaction chamber with the decarboxylation of the *cannabis*/hemp plants before or after the extraction/concentration in the same reaction chamber, thus drastically reducing the processing time and costs.

Furthermore, the present invention is directed to a system for extracting and infusing cannabinoids in a carrier oil which uses either green or dried whole *cannabis*/hemp plant, to maintain the full spectrum of the therapeutically desirable compounds in their naturally occurring proportions.

Further, the present invention is directed to an enhanced oil extraction/concentration system which produces sterile concentrated full spectrum infused hemp/CBD oil which can be safely stored for long periods of time (possibly, years) until it is ready for final processing (pressing, filtration, dilution, and final product packaging).

The present invention is also directed to an enhanced oil extraction/concentration method capable of removing trace heavy metals and other undesirable compounds, potentially detoxifying the *cannabis*/hemp plant material during extraction/infusion processing, so that no post-extraction detoxification of the infused oil is required.

Additionally, the present invention is directed to a system for cannabinoids extracting and infusing in a carrier oil requiring inexpensive equipment and reduced operating costs which are less expensive than that of typical super-critical $CO_2$ or ethanol based extraction, and which does not require advanced chemical processes to perform direct oil extraction and concentration.

BACKGROUND OF THE INVENTION

Cannabidiol, or CBD, is one of the many cannabinoids found in the hemp plant, *Cannabis indica*. Industrial hemp differs from marijuana, because it has little (<0.3%) of tetrahydrocannabinol (THC), and contains high concentrations (10-16%) of Cannabidiol (CBD). Without the THC there are no psychoactive effects in the derived medicinal substances. Unlike other varieties of *cannabis* which are federally illegal to grow, industrial hemp can now be legally grown due to a provision in the recent Farm Bill of 2018 and recent changes in legislation of each individual state. As a result of these legal changes, the US CBD industry has exploded. It grew by yearly 40% in 2017 to reach total sales of $367 million. This trend is projected to continue and should exceed more than $500 million in sales during 2018.

The surge in CBD sales is due to its success in treating a variety of medical diseases, many of which are otherwise untreatable. CBD can be used as a substitute for some prescription medications. The list of diseases that are responsive to CBD continues to grow. Some of these include pain relief for the chronic pain from arthritis, multiple sclerosis and Fibromyalgia. It may be beneficial for treating anxiety, depression and post-traumatic stress disorder. CBD can reduce cancer-related pain and the side effects of chemotherapy including nausea and vomiting. CBD has been shown, in laboratory and animal studies, to have anticancer properties. It reduces the frequency of epileptic seizures and reduces symptoms from Parkinson's disease. CBD can treat acne via its anti-inflammatory properties. CBD lowers blood pressure in humans and reduces impact of ischemic heart disease in diabetic mice. CBD can lessen the severity of withdrawal in patients undergoing detoxification from opioids.

There is increasing evidence that CBD-based therapies may be greatly effective when the full spectrum of therapeutic compounds found in the hemp plant is used. *Cannabis* researchers have come to recognize the importance of using a whole hemp plant to produce the "Entourage Effect" which was described in 1998 by S. Ben-Shabat and Raphael Mechoulam to explain the complex interactive synergy that occurs between *cannabis* compounds.

So far, more than 90 cannabinoids, 200 terpenes and 20 flavonoids have been identified and this number continues to rise. Many of these compounds are only present in trace quantities. Exactly how all of these phytocannabinoids interact within the human body's endocannabinoid system is not fully understood. For example, Marinol (which is the FDA approved synthetic tetrahydrocannabinol, or THC) proved to be ineffective for relieving the nausea associated with chemotherapy used to treat cancer in cancer patients. However, when these cancer patients were given "whole plant marijuana", their nausea resolved. Thus, it may be advantageous to preserve the full spectrum of all of the therapeutically desirable compounds found in whole hemp plants.

The current extraction methods conventionally focus on isolating only the THC and/or CBD, often at the expense of other trace compounds. Recognition of the advantages of the "full spectrum" therapy has led to an increasing number of products that strive to retain as many of the cannabinoids, terpenes and the flavonoids, as possible. These compounds are chemically fragile and must be gently extracted from the

*cannabis* plant. Careful extraction is needed to preserve the cannabinoids, terpenes and the flavonoids as they exist in the native cannabinoid plant.

Numerous methods have been developed which address preparation of medicinal compounds from *cannabis*/hemp plant.

For example, hydrocarbon extraction method uses a variety of organic solvents to extract the cannabinoids from the plant. In one of the most iconic approaches developed by Rick Simpson in 2003, he successfully treated his own basal cell carcinoma by extracting THC and CBD from an Indica strain of *cannabis* and concentrating it into a thick paste. In the method, the plant is crushed and stirred into an organic solvent such as isopropyl alcohol, ethanol, butane, or naphtha. All of these are volatile solvents and vaporize while the concentrate is slowly heated. The highly concentrated paste is drawn up into a syringe and is dispensed to the patient in small doses three times a day.

A drawback of this approach is that the solvents used in the method are flammable and combustible. If ingested in large quantities, they are highly toxic.

Another hydrocarbon approach uses butane or propane to extract the cannabinoids into butane hash oil. The cannabinoid plant material and liquid butane are combined in a pressurized and heated system. The residual butane solvent is subsequently removed under vacuum. This process results in a clear sticky rosin that includes high concentrations of THC, CBD and Terpenes. However, there is a serious risk of explosion due to the combustible nature of the butane. Thus, the method requires an additional stage of the butane recycling. Typically, patients refuse to ingest medicine that contains even trace levels of butane.

Ethanol extraction is another process developed to extract important compounds from the *cannabis* plant. Distilled ethanol is added to a container of *cannabis* to react for at least one hour. The resulting mixture is subsequently filtered to separate the solids from the ethanol solution which is now loaded with cannabinoids and Terpenes. The saturated ethanol solution is boiled in order to remove the ethanol and to concentrate the cannabinoids. Various strategies are used to condense the ethanol vapor to recover the ethanol, so that it can be recovered and return into the process for multiple extraction cycles. The method is relatively rapid and efficient, and is suitable for large scale operations. It is generally faster than supercritical $CO_2$ extraction methods.

Ethanol extraction has a high level of extractive power, which allows it to remove undesirable compounds including chlorophyll and the waxes. Unfortunately, this extractive power is also undesirable as it removes valuable compounds such as monoterpenes and sesquiterpenes, which are also removed and wasted during the evaporation of the ethanol. The systems adapted for the ethanol extraction method are quite costly with the costs typically running in the hundreds of thousands of dollars for an industrial capacity system.

Supercritical $CO_2$ (SC $CO_2$) extraction process is currently the most popular technology for processing legal *cannabis* and hemp. $CO_2$ is a highly efficient extraction method. The method works by placing $CO_2$ under very high pressure (~1080 PSI) and temperature (~88° F.) to reach the so-called critical point. Any increase above these levels results in a "supercritical fluid", which is a unique state of matter where the liquid can move through a solid matter as if it was a gas and at the same time be soluble in a liquid. There is a considerable variability between the temperature and pressure ranges that different extractor facilities use for the process. The temperatures may range from 45° C. to 60° C. (113° F. to 140° F.) and the pressures can range from 3000 PSI to 5000 PSI. The conditions used can affect the quality and yield of the cannabinoids, terpenes and flavonoids. For example, using a higher extraction temperature will decrease the yield of Terpenes in the extract. Higher levels of a temperature also run the risk of denaturing the products and increase the amount of extracted wax and resin. Increasing the pressure will increase the amount of chlorophyll poured into the extract. $CO_2$ extraction produces high concentrations of THC and CBD but at the expense of losing CBN and the terpenes. A comparative study conducted in Washington State University analyzed the cannabinoid and terpene concentrations before and after SC $CO_2$ extraction performed on common *cannabis* chemo-types. The concentration of THC and CBD increased significantly in the final extract. However, there was a significant reduction in the terpenes following extraction. Monoterpenes such as D-limonene and alpha-pinene were found at lower levels than the original *cannabis* sample. These monoterpenes have lower vapor pressures and may have been evaporated in the super critical state. This reduction in the monoterpenes after SC $CO_2$ extraction alters the terpene fingerprint of the plant. This may undesirably alter the interaction and synergy between the cannabinoids and Terpenes, i.e., undermine the Entourage effect.

A SC $CO_2$ process is presented in International PCT Publication WO2016/153347 which is directed to a cannabidiol isolate from industrial hemp for use in pharmaceutical and/or cosmetic preparations. The industrial hemp material is subjected to a treatment resulting in a reduction of the particle size, such as cutting or grinding. The extraction step comprises contacting the industrial hemp with supercritical $CO_2$. Typically, the hemp material is placed in a pressure vessel following which supercritical $CO_2$ is passed into the vessel. The supercritical $CO_2$ is preferably maintained at a temperature of 35-120° C., most preferably at a temperature of 40-100° C. In the process, the supercritical $CO_2$ is preferably at a pressure of 100-350 bar, most preferably at a pressure of 150-300 bar.

In order to obtain the crude extract, $CO_2$ containing dissolved compounds is typically collected in a vessel where the pressure is lowered so that the dissolved compounds precipitate to form the crude extract. Typically, for this purpose the $CO_2$ containing dissolved compounds is transported to a separator vessel, where the pressure is lowered, and the dissolved compounds precipitate to produce the crude CBD extract.

Since the industrial hemp material from which CBD is to be prepared typically contains significant amounts of the cannabidiol acid CBD A, the plant material or crude extract is subjected to a decarboxylation step to convert CBD A to CBD. Decarboxylation is preferably carried out by heating the CBD A containing material to a temperature within the range of 90-130° C., more preferably within the range of 100-120° C.

The crude CBD extract is subjected to thin film evaporation to produce a refined extract. Thin film evaporation is preferably performed at a temperature within the range of 100-160° C., more preferably within the range of 120-140° C. Preferably, thin film evaporation is performed at a pressure within the range of $8 \times 10^{-2}$-$1 \times 10^{-3}$ mbar, preferably within the range of $6 \times 10^{-2}$-$1 \times 10^{-3}$ mbar.

The main advantage of the SC $CO_2$ extraction is safety, since it is non-flammable, and is safer than the hydrocarbons or ethanol extraction methods. It only leaves behind minute quantities of $CO_2$ solvent residue, which quickly evaporates at room temperature.

Its principle disadvantage however, in addition to failing to produce a full spectrum substance and losing the terpenes and the minor cannabinoids during the extraction, is an extremely high cost. A typical large-scale unit can cost from $300,000-$10 million.

Disadvantageously, the current extraction methods for isolating and concentrating THC and CBD use a solvent of some kind, e.g. butane, isopropyl alcohol, naphthalene, ethanol or supercritical $CO_2$. The solvent extracts and concentrates the lipophyllic cannabinoids from the *cannabis*/hemp plant. The *cannabis* extracts obtained with the use of solvents have an unpleasant taste and are unpalatable. To make the *cannabis* extract more palatable, it is transferred into an edible product or capsulated to mask the unpleasant taste and for an easier ingestion. The concentrated extract is transferred into an appropriate carrier, such as MCT oil or ethanol, and is subsequently diluted to a proper concentration. This final carrier solution is used to prepare tinctures, hemp oil, gummies, candy, capsules or sub lingual sprays. An exception to this approach is Rick Simpson oil, which can be consumed without an enhancement to improve the taste.

The extraction solvents used in the conventional extraction methods, serve as a "middleman" in the cannabinoid extraction and concentration process. It would be highly desirable to eliminate solvents from the extraction process and to extract and concentrate the whole hemp plant, all of the cannabinoids, terpenes and flavonoids, directly into the final carrier oil/substance, so that the "extracting" carrier oil/substance would now be the final product without the requirement for post-extraction/concentration solvent residuals removal and additional processing for improving palatability and ingestion purposes. The carrier oil/substance concentrate would be merely diluted (to the proper concentration) and packaged as a consumable product, such as tinctures, hemp oil, gummies, candy, capsules, or sub lingual sprays.

As an example of the solvents-based cannabidiol extraction methods, in U.S. Pat. Nos. 10,308,625 and 9,950,275, after cleaning and grinding a root ball, the ground plant material is frozen, and, as customarily in the conventional methods, a solvent is added to the dry powder to produce a mixture. This mixture is poured through a sieve, such as cheese cloth material, to remove any suspended particles. The "purified" mixture is collected. In one embodiment, the "purified" mixture is subjected to heat while in a container for evaporating the solvent. In order to obtain CBD, the heat of less than 120 degrees Fahrenheit is applied. A desired cannabinoid is condensed and subsequently collected.

A different approach for extracting CBD, THC, and other compounds from *cannabis* is presented in U.S. Pat. No. 10,011,804 which uses a controlled cavitation. This method includes drying the plant, grinding or chopping the plant, mixing the resulting pieces of the plant with a solvent to form a mixture, circulating the mixture through a controlled cavitation reactor to liberate CBD, THC, desirable oils, and other compounds from the pieces, and separating the liberated CBD, THC, desirable oils, and other compounds from the fluid.

The controlled cavitation device includes a housing within which a rotor can be rotated at a preselected and controllable speed by motor. Rotation of the rotor within the controlled cavitation device as the mixture is pumped through the cavitation zone induces highly energetic cavitation events in the mixture. These cavitation events induce highly energetic shock waves and corresponding highly intense and rapid pressure fluctuations that propagate through the mixture within the cavitation zone. This environment liberates CBD, THC and other oils and compounds from the *cannabis* pieces within the mixture and these compounds become dissolved or entrained within the fluid of the mixture. Upon leaving the controlled cavitation device, the mixture flows through conduit, through a heat exchanger for removing heat generated by the cavitation process, and through additional conduits back to the reservoir tank.

None of the conventional extraction methods are based on the concept of a solvent-free processing of a whole *cannabis*/hemp plant for extraction and concentration of full spectrum of cannabinoids, terpenes and flavonoids at their naturally occurring proportions directly into a final carrier oil/substance product using thoroughly controlled temperature/pressure within the reaction chamber.

It would be highly desirable to provide a method that gently extracts the full spectrum of phyto-cannabinoids, terpenes and the flavonoids from a whole *cannabis*/hemp plant without solvents to directly infuse these therapeutically desirable substances into the carrier oil using thoroughly controlled pressure and temperature reaction regime.

SUMMARY OF THE INVENTION

It is therefore an object of the present invention to provide an enhanced solvent-free system for gently extracting the phyto-cannabinoids, terpenes and the flavonoids from a *cannabis*/hemp plant and simultaneously infusing them into carrier oil using precisely controlled pressure/temperature reaction regime favorable for the therapeutically desirable substances and the carrier oils.

It is another object of the present invention to provide a system for fabricating medicinal compounds from *cannabis*/hemp plant which prevents the inadvertent loss of the desirable therapeutic components of the plant (including phyto-cannabinoids, terpenes and flavonoids) which may happen due to vaporization at excessive reaction temperatures. By retaining these therapeutic compounds in their naturally occurring proportions, a concentrated full spectrum infusion oil can be produced with the preserved synergy of the Entourage Effect.

It is contemplated that the subject method and system may be carried via the fabrication steps beginning with grinding the *cannabis*/hemp plant into fine particles using a rotating blade, a Hammer mill, or grinder.

Optionally, the finely processed plant material is decarboxylated in an oven at 200°-260° F. for about one hour. The decarboxylation stage may be alternatively applied to the final product by performing the post-extraction decarboxylation.

Subsequently, the finely processed plant material and a predetermined volume of the carrier oil of choice are entered into one or more enclosed extraction vessel(s) that is (are) subsequently tightly sealed. The extraction vessel(s) can be fabricated from a glass, plastic, metal or other materials.

Optionally, a stirring mechanism (in the form of a rotating magnetic bar, stirring paddle or jets of air or oil) may be included in each extraction vessel to mix and agitate the finely processed plant material with the carrier oil.

In one embodiment, multiple extraction vessels may be simultaneously placed into the pressure reaction chamber (reactor). Each extraction vessel can be equipped with a cover capable of tight sealing and having a vent for maintaining equilibrium between the pressure in the reactor and in the extraction vessel.

The subject method further continues with closing and tightly sealing the pressure reaction chamber. Subsequently, an elevated pressure and increased reaction temperature are established in the pressure reaction to elevate the boiling point of the water/moisture in the plant material which allows enhanced diffusion of the phyto-cannabinoids, terpenes and the flavonoids into the carrier oil at an enhanced rate. Undesirable plant components, such as cellulose, hemicellulose, and lignin, are formed of large particles and remain as insoluble solids. The enhanced pressure allows the reaction to proceed 30% faster and with 50-75% less energy.

In the present method, the pressure is typically elevated to the level ranging between 11 PSI and 15 PSI. The elevated reaction temperature ranges from 230° F. to 250° F., but not higher to maintain the reaction temperature below the boiling points of the majority of the cannabinoids and terpenes, as well as the carrier oil(s) in order to preserve these substances in the final infusion oil product.

The enhanced temperature and pressure gradient in the extraction vessel(s) drive the cannabinoids, flavonoids and terpenes into the carrier oil directly without requiring any intermediate solvent thus providing the "solvent-free" extraction method.

Subsequently, the reaction chamber is allowed to cool. The contents of the extraction vessel(s) are poured into a special press that in one iteration compresses the infused oil through a plate that has properly sized holes for passage of the infused oil, while leaving the undesirable plant material behind. In another iteration, the contents of the extraction vessel(s) are poured into a screw press with an auger that has variable-sized flights that compress the extract in such a way to express the infused oil out through properly sized holes on the sides and into collection tray, while forcing the undesirable solids out through the distal opening at the end of the auger shaft into a collection container. The compressed oil is subsequently filtered either by passage through a fine filter cloth (with openings of approximately 5-200 microns), a screen, an automated oil cleaner/filter, a sedimentation tank or filter aids to remove residual sediment or waxes.

Alternatively, the hermetically sealed extraction vessel containing the infused oil final product can be stored, as a whole, for a short or long period of time.

The above-presented method for preparing a full spectrum *cannabis*/hemp medicinal compound containing phyto-cannabinoids, terpenes and flavonoids in naturally occurring proportions found in *cannabis*/hemp plants preferably uses whole hemp plants, green (freshly harvested) or dried hemp plant.

The carrier oil is the oil that helps preserve the potency and delivery of the active compounds within the final product. It is of importance that the carrier oils used in the subject method have a high smoking point. The extraction vessels may be filled with the same carrier oil, or extraction vessels may be filled with different carrier oils. In the subject method, the carrier oils may include an oil selected from the coconut oil, Medium-chain triglyceride (MCT) oil, cold-pressed hemp oil, extra virgin olive oil (EVOO), black cumin oil, frankincense oil, etc.

In another aspect, the present invention constitutes a system for preparing a full spectrum *cannabis*/hemp medicinal compound containing phyto-cannabinoids, terpenes and flavonoids in naturally occurring proportions found in *cannabis*/hemp plants.

The subject system includes a hemp plant entrance station to produce hemp plant fine particles material. Such entrance station may be in the form of a grinder, a mill, or some other mechanism capable of processing plant to produce fine particles hemp plant material.

A pressure reaction chamber (also referred to herein as a reactor) is coupled to the entrance station to receive therefrom the fine particles hemp plant material. The reactor is formed from a material (for example, stainless steel) capable of withstanding an elevated pressure of 15 PSI. The reactor also is provided with means for hermetical sealing.

One or several extraction vessels, each capable of being hermetical sealed, is (are) installed in the reactor. The extraction vessels have a lid capable of hermetical sealing. A valve can be installed in the lid or a side wall of the extraction vessel to provide environmental (pressure/temperature) equilibrium between the interior of the reactor and the interior of each extraction vessel.

The extraction vessels may be interconnected in sequence to provide a pressure/temperature equilibrium therebetween. Alternatively, each extraction vessel can have an individual exit piping for dislodging of the final infused oil product. The individual exit pipes may be connected in a manifold type connection to form a collective exit for the final product from the reactor.

The extraction vessels receive a predetermined amount of carrier oil and the hemp plant fine particles material. Mixing mechanism nay be provided in each extraction vessel to mix the fine particles of the hemp plant with the carrier oil.

When the reactor and the extraction vessels are sealed, the pressure and the reaction temperature in the reactor are elevated to a predetermined level (about 15 PSI pressure and about 230-246 F temperature).

Phyto-cannabinoids, terpenes and flavonoids are extracted from the hemp plant material in a solvent-devoid manner by exposing the hemp plant fine particles in each sealed extraction vessel to a reaction temperature maintained below a boiling point of each of the phyto-cannabinoids, terpenes, and flavonoids, as well as the carrier oil. The extracted phyto-cannabinoids, terpenes and flavonoids are diffused into the carrier oil at an enhanced rate, thus producing the final infused oil product.

The subject system may be equipped with a storage stage operatively coupled to the exit of the reactor. The exit piping of the extraction vessels (either in a collective implementation or individually) enters the storage stage to output therein the final infused oil product from the reactor chamber. The final infused oil product is a concentrated solvent-free detoxified full spectrum infused oil which can be stored in the storage stage for a short time or the long term (years, if needed).

The subject system also includes a final processing stage which may include a pressing unit, a filtration unit, as well as a dilution and packaging units. At the pressing unit, the output infused oil is compressed through a plate formed with openings dimensioned to pass the infused oil while retaining some unwanted solids. At the following filtering unit, the compressed oil is filtered through a fine filter cloth to retain residual sediment from the compressed infused oil.

The subject system further includes an oven adapted for decarboxylating procedure. It may be installed before the reactor for pre-extraction decarboxylating the hemp plant fine particles in the oven at a temperature ranging from 200 F to 260 F for a time period of about one hour. Alternatively, or in addition to the pre-extraction decarboxylating unit, the oven may be installed coupled to the output of the reactor for post-extraction decarboxylation of the infused oil final product.

These and other objects and advantages of the subject inventive concept will be more apparent from the following detailed description of the preferred embodiment (s) when taken in conjunction with the Patent Drawing Figure(s) presented in the subject Patent Application.

DETAILED DESCRIPTION OF THE PREFERRED EMBODIMENT(S)

Referring to the FIGURE, the subject system 10 is developed for supporting the method for preparing a full spectrum *cannabis*/hemp medicinal compound containing phyto-cannabinoids, terpenes and flavonoids in naturally occurring proportions found in *cannabis*/hemp plants. The system 10 includes a hemp plant entrance station 12 which receives, at the input 14, whole hemp plant(s) either freshly cut (green) or dried. The hemp plant(s) follows to a grinding stage 16 of the entrance station 12 to expose the hemp plant(s) to an operation resulting in production of hemp plant fine particles material 18. The grinding station 16 may be implemented in the form of a grinder, a mill, or some other mechanism capable of processing plant to produce fine particles hemp plant material 18.

The fine particles hemp plant material 18 is further transported (either manually or by a conveyor belt, or some other transporting mechanism) to a pressure reaction chamber (also referred to herein as a reactor) 20 which is operatively coupled at its entrance 22 to the grinding station 16 to receive therefrom the fine particles hemp plant material 18.

The reactor 20 is formed from a material (for example, stainless steel) capable of withstanding an elevated pressure of 15 PSI. The reactor 20 also is provided with means for hermetical sealing the reactor to retain a reaction pressure inside of the reactor 20.

One or several extraction vessels 24 (also referred to herein a reaction vessel), each capable of being hermetical sealed, is (are) installed in the reactor 20. The extraction vessels 24 are equipped with a lid 26 which can have a specific design capable of hermetical sealing the extraction vessel 24. This may be an adjustable lid on each reaction vessel 24 to allow for equilibration of the pressure between the larger reaction chamber 20 (that contains a number of reaction vessels 24) and the interior of each reaction vessel 24. This can be mediated, for example, either by a "2-piece" lid with a plate that is deflectable or by the insertion of a pressure sensitive release valve 28 into the lid of each reaction vessel.

The valve 28 can be installed in the lid 26 (or, alternatively, in a side wall 30 of the extraction vessel 24) to support a pressure equilibrium between the inside of the reactor 20 and the inside of each extraction vessel 24.

The extraction vessels 24 may be interconnected in sequence through a piping 32 to provide pressure/temperature equilibrium between them. Alternatively, each extraction vessel 24 can have an individual exit pipe 34 for dislodging the final infused oil product 36. The individual exit pipes 34 may be interconnected in a manifold type connection to form a collective output 38 for unloading of the final product 36 from the reactor 20.

The extraction vessels 24 receive a predetermined amount of a carrier oil 40 and the hemp plant fine particles material 18. A mixing mechanism may be provided in each extraction vessel 24 to mix the fine particles 18 of the hemp plant with the carrier oil 40.

The carrier oil is a substance that enhances the preservation properties, potency and delivery of the active compounds within the final product. It is of importance that the carrier oils 40 used in the subject method have a high smoking point so that the reaction temperature in the pressure reaction chamber 20 does not cause burning of the carrier oil filled in the extraction vessels 24. The extraction vessels 24 may be filled with the same carrier oil 40. Alternatively, the extraction vessels 24 may be filled with different carrier oils.

In the subject method, the carrier oil(s) may be used which are selected from numerous carrier oils compatible with the particular process of the subject method. The carrier oil 40 may be one of the coconut oil, Medium-Chain Triglyceride (MCT) oil, cold-pressed hemp oil, extra virgin olive oil (EVOO), black cumin oil, Frankincense oil, or their combinations.

The subject system 10 further includes a pressure source, for example, a pump 60, a heater 62, and a cooling unit 64, each operatively coupled to the reactor 20. When the reactor 20 is tightly (hermetically) sealed, the pressure and the reaction temperature in the reactor 20 are elevated (by operating the pump 60 and the heater 62, respectively) to a predetermined level (about 15 PSI pressure and about 230° F.-250° F., preferably, 246° F., temperature). The combination of such pressure and reaction temperature provides the extraction conditions inside the reactor 20 (as well as in the extraction vessels 24) favorable for the intensive process where the phyto-cannabinoids, terpenes and flavonoids are extracted from the hemp plant material 18 in a solvent-devoid manner. The extracted phyto-cannabinoids, terpenes and flavonoids are diffused into the carrier oil 40 at an enhanced rate, thus producing the final infused oil product 36 free of solvents residues and in a very efficient manner.

The subject system 10 may be equipped with a storage station 42 operatively coupled to the output 44 of the reactor 20. The exit piping 38 of the extraction vessels 24 may be contemplated either in a collective implementation (exit pipes 38) or as individual pipes 34.

Figure 1:
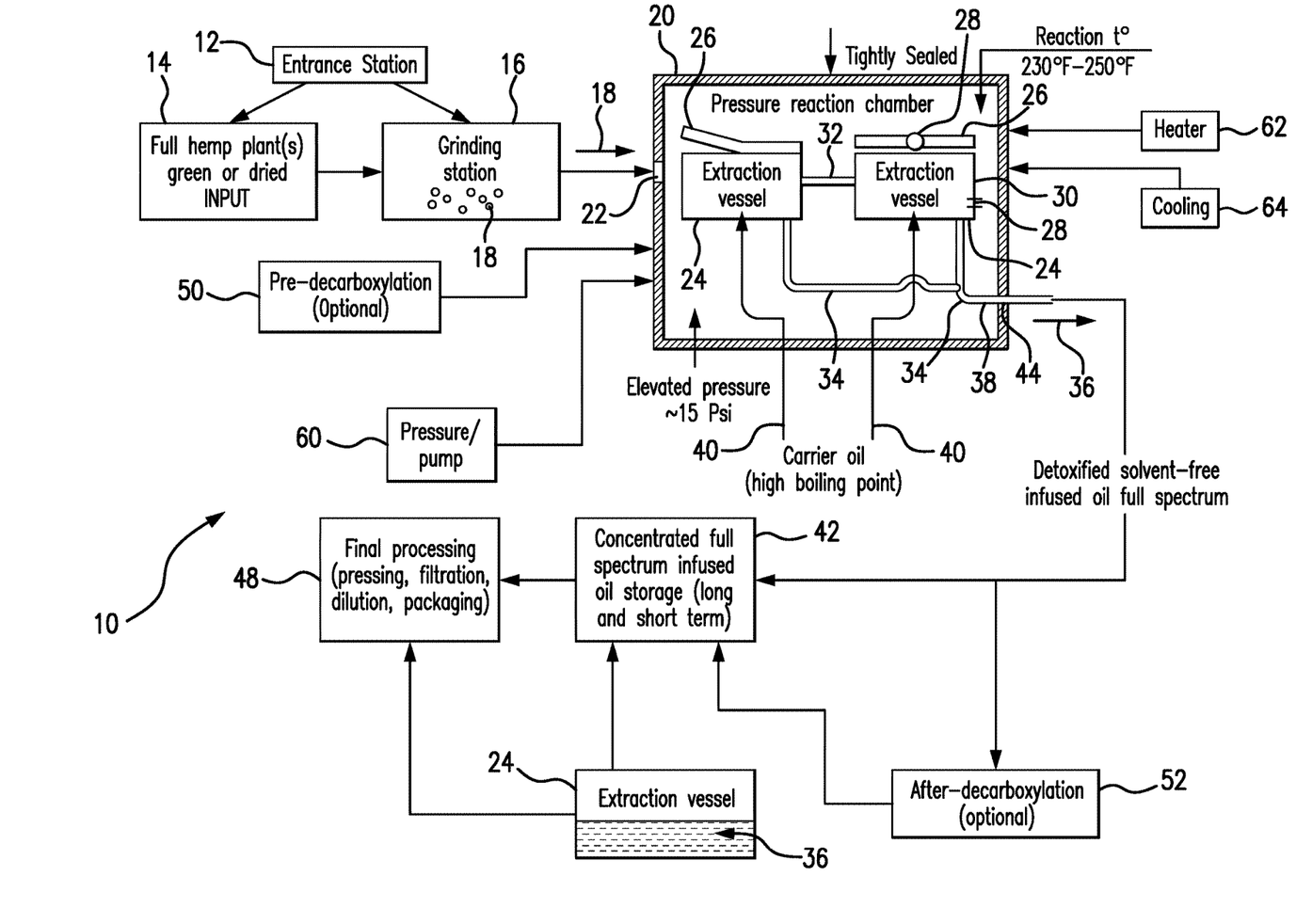
The FIGURE is a flow chart representative of the subject solvent-free process for extraction and concentration of full spectrum CBD and other cannabinoids in a carrier oil.

The infused oil final product 36 is a concentrated solvent-free detoxified full spectrum infused oil which can be stored in the storage station 42 for a short time or the long term (years, if needed). After the reactor 20 is cooled (either naturally or forcefully by a cooling unit 64), the infused oil final product 36 contained in the extraction vessels 24 can be unloaded therefrom into a container at the storage station 42 through the exit piping 38. Alternatively, as also shown in FIG. 1, the extraction vessel 24 containing the infused oil final product 36 and hermetically sealed to retain the contents therein, can be removed from the reactor 20 and transferred to the storage station 42, as a whole, for a short term storage or a long term storage.

The subject system 10 also includes a final processing stage 48 which may include a pressing unit, a filtration unit, as well as a dilution and packaging units. At the pressing unit, the infused oil final product 36 (either delivered from the extraction vessels 24 upon the extraction/infusion process is over, or from the storage station 42 after a desired storage period of time) is compressed through a plate formed with openings dimensioned to pass the infused oil while retaining some unwanted solids. At the following filtering unit, the compressed oil is filtered through a fine filter cloth to retain residual sediment from the compressed infused oil.

The subject system further includes an oven adapted for decarboxylating procedure. The oven 50 may be installed between the entrance station 12 and the reactor 20 for pre-extraction decarboxylating the hemp plant fine particles in the oven 50 at a temperature ranging from 200° F. to 260° F. for a time period of about one hour. Alternatively, or in addition to the pre-extraction decarboxylating unit, the oven 52 may be installed coupled to the output 44 of the reactor 20 for post-extraction decarboxylation of the infused oil final product 36.

When designing the subject effective method for extracting and separating the desirable components (phyto-cannabinoids, terpenes and the flavonoids for mediating the desired therapeutic effects) from the undesirable ones (cellulose, hemicellulose and lignin) in the hemp plant, the effect of the solubility and boiling point temperature of the various components within the chamber 20 where the reaction occurs have been considered. Specifically, there are numerous compounds found in the whole hemp plant including the phytocannabinoids which include: Δ-9-tetrahydrocannabinol (THC), cannabidiol (CBD), cannabinol (CBN), cannabichromene (CBC), cannabigerol (CBG), Δ-8-tetrahydrocannabinol (Δ-8 THC) and tetrahydrocannabivarin (THCV). Their boiling points range from 314° F. to 428° F. (157° C.-220° C.). There are also more than 200 aromatic terpenes isolated from the whole hemp plant. Some of these include: α-pinene, linalool, myrcene, limonene, B-caryophyllene, humulene, bisabolol, ocimene, valencene, terpinolene, geraniol, α-terpineol, nerolidol, phytol and pulegone. Their boiling points range from 246.2° F. to 435.2° F. (119° C.-224° C.). The flavonoids, which have boiling points that range from 273.2° F. to 482° F. (134° C.-250° C.), are also representatives of the active compounds in the *cannabis*/hemp plant. When the afore-listed components are brought together in proper proportions (preferably, as exist naturally in the *cannabis*/hemp plant), they work together in a synergetic manner with enhanced therapeutic effects. This synergetic phenomenon is known as the Entourage Effect.

Most of the hemp plant (by weight) is composed of undesirable components. These undesirable components must be isolated and removed from the *cannabis*/hemp plant in order to create a useful product with therapeutic benefits. By dry weight, the plant contains 73-77% w/w cellulose, 7-9% w/w hemicellulose and 4-6% w/w lignin, while the hemp shives contain 48% w/w cellulose, 21-25% w/w hemicellulose and 17-19% w/w lignin.

The desirable active ingredients of the *cannabis*/hemp plant are all lipid soluble. Once they are separated from the plant material, they are usually dissolved in an organic solvent such as ethanol or medium chain fatty acid carrier oil. Some popular carrier oils include: coconut oil, olive oil, avocado oil, almond oil, canola oil, flax oil, grapeseed oil, peanut oil, safflower oil, sunflower oil, walnut oil and butter.

When transferring lipid soluble compounds into organic oils at an elevated temperature, the "smoke point" of the chosen oil is to be taken in consideration. The smoke point refers to the temperature at which oil starts to burn and smoke. For example, the smoke point of coconut oil is 350° F., while the smoke point of olive oil ranges from 410° F. to 468° F.

Fortunately, the undesirable components (cellulose, hemicellulose and lignin) have limited solubility in carrier oils, due to their large molecular size and complex structure. As a result, even under elevated temperature or pressure, the undesirable components remain intact as a solid and do not enter into the carrier oil.

Conversely, the therapeutic compounds are all lipid soluble. Altering the temperature and pressure within the reaction chamber 20 can enhance the diffusion of lipid-soluble compounds into the carrier oil 40 of choice.

Increasing the temperature of a compound increases its kinetic energy. The higher kinetic energy increases the motion of its molecules, breaking intermolecular bonds in the solids, thus causing the molecules to escape from the solids, increasing their solubility and ability to enter into the target solution (carrier oil). Thus, by elevating the reaction temperature, the solubility of the phyto-cannabinoids, terpenes and flavonoids is also increased so that these compounds are easily infused into a carrier oil, to produce a carrier-oil that has a high concentration of these active compounds.

However, the limitations exist on increasing the reaction temperature to enhance solubility of the desired active compounds and their concentration in the carrier oil. Specifically, the reaction temperature cannot exceed the boiling point of the desirable active compounds and the carrier oil. If the reaction temperature exceeds the boiling point of a given phyto-cannabinoid, terpene or flavonoid, they will vaporize into the atmosphere and be wasted from the final product. If the reaction temperature in the reactor exceeds the smoke point of the carrier oil, the taste of the final product would be unpleasant, For this reason, it is desirable to keep the reaction temperature below 250° F., preferably below 246° F. By carefully controlling and keeping the reaction temperature below this temperature point, a "full spectrum" infusion oil can be produced that contains the majority of the active components (phyto-cannabinoids, terpenes and the flavonoids) found in the whole hemp plant.

Increasing the pressure has little effect on the liquids and solids in the reactor. However, increased pressure forces more of the gas molecules (especially water vapor) into solution, increasing their solubility as governed by Henry's Law of Gases. Even "dried" *cannabis*/hemp plant material contains a significant amount of water (14-20%). Elevating the pressure inside a tightly sealed reactor chamber to 15 PSI (above local atmospheric pressure), increases the boiling point of water from 212° F. to 250° F. 12 At a lower pressure of, for example, 11.5 PSI, the boiling point of water is only elevated from 212° F. to about 243° F. This temperature is below the boiling points of most of the valuable phyto-cannabinoids, terpenes and the flavonoids.

This combination of the enhanced pressure and elevated reaction temperature used in the subject method results in the reaction capable of proceeding about 30% faster and with 50-75% less energy consumption.

In addition to the above-presented advantages attained in the subject system/method, the subject enhanced oil extraction/concentration is performed on the equipment that is much less expensive than the conventional ethanol extraction or supercritical $CO_2$ extraction methods. The subject system/method are flexible enough to either process small batches of *cannabis*/hemp plant material or be scaled-up to handle 1000s of pounds of *cannabis*/hemp per day. In addition, a single reactor chamber can be used to perform multiple tasks on the *cannabis*/hemp plant material which does not have to be transferred into another container. For example, the *cannabis*/hemp can be decarboxylated before or after the enhanced oil extraction/concentration in the same reaction chamber.

The subject system/method do not require advanced chemical processes of laboratory levels and thus the equipment and operating costs are lower than that of the supercritical $CO_2$ or ethanol extraction.

Another advantage results from the fact that no solvents are used in the extraction/concentration process. Therefore, no residual solvent is present in the final full-spectrum hemp/CBD oil product, and there is no need for detoxification from the solvent residue or for post-extraction taste enhancing processing. The subject enhanced oil extraction/concentration method is capable of removal trace heavy metals and other undesirable compounds, potentially detoxifying the *cannabis*/hemp plant material during extraction stage.

Furthermore, the subject oil extraction/concentration method can process either green or dried *cannabis*/hemp plant material (using slightly different reaction time and conditions). The ability to process freshly harvested/green *cannabis*/hemp offers a substantial advantage over alternative conventional extraction methods that can only be performed on the dried material (moisture 12-16%). Being able to process green plant material, the subject system/method can avoid the drying stage and storage steps. Green plant processing used in the subject system/method bypasses the expensive, energy intensive and time consuming "bottlenecks" in the harvesting and processing process. Immediate processing of the green *cannabis*/hemp plant may reduce the need for drying equipment, save energy and reduce the amount of warehouse space that is required to store and dry the *cannabis*/hemp plants in conventional approaches.

Moreover, another important feature of the subject system/method is the ability to produce a sterile batch of hemp/CBD oil within a sealed container (extraction vessel 24, and/or the storage container 42). The sealed container can be safely stored for long periods of time (possibly years) until it is ready for final processing (pressing, filtration, dilution, and final product packaging) at the final processing station 48.

The subject method gently extracts a full spectrum of the phyto-cannabinoids, terpenes and the flavonoids from a *cannabis*/hemp plant and directly infuses them into a carrier oil using precisely controlled, enhanced pressure and temperature regime. This process prevents the inadvertent loss of the desirable therapeutic components of the hemp plant due to vaporization at excessive reaction temperatures. By retaining the active therapeutically desirable compounds in their naturally occurring proportions available in whole hemp plants, concentrated full spectrum infusion oil with the preserved synergy of the Entourage effect is produced in the efficient and expedited manner.

Although this invention has been described in connection with specific forms and embodiments thereof, it will be appreciated that various modifications other than those discussed above may be resorted to without departing from the spirit or scope of the invention as defined in the appended claims. For example, functionally equivalent elements may be substituted for those specifically shown and described, certain features may be used independently of other features, and in certain cases, particular locations of elements, steps, or processes may be reversed or interposed, all without departing from the spirit or scope of the invention as defined in the appended claims.

What is claimed is:

1. A system for preparing a full spectrum *cannabis* extract containing phyto-cannabinoids, terpenes and flavonoids, comprising:
    an entrance station equipped with a grinding mechanism for processing hemp plant material to produce hemp plant fine particles material,
    at least one hermetically sealable extraction vessel operatively coupled to said entrance station to receive therefrom said hemp plant fine particles material,
    a carrier oil contained in said at least one extraction vessel,
    a hermetically sealable pressure reaction chamber, said at least one extraction vessel being installed in said pressure reaction chamber,
    an environmental equilibrium mechanism established between interiors of said at least one extraction vessel and said pressure reaction chamber,
    a pressure source operatively coupled to said pressure reaction chamber operating to establish an elevated pressure ranging from about 11 PSI to 15 PSI in said hermetically sealed pressure reaction chamber,
    a heater operatively coupled to said pressure reaction chamber for creating and maintaining a reaction temperature in said hermetically sealed pressure reaction chamber A at a level above 230 F and below a boiling point of each of said phyto-cannabinoids, terpenes and flavonoids and below a smoke point of said carrier oil,
    wherein by exposing said hemp plant fine particles material and said carrier oil in said at least one extraction vessel to said elevated pressure and said reaction temperature established in said sealed pressure reaction chamber, enhanced reaction conditions are established in said at least a first extraction vessel for solvent-free extraction of said phyto-cannabinoids, terpenes and flavonoids from said hemp plant fine particles material and for diffusing of the extracted phyto-cannabinoids, terpenes and flavonoids into said carrier oil at an enhanced rate, thus producing an infused oil final product containing full spectrum phyto-cannabinoids, terpenes and flavonoids in naturally occurring proportions.

2. The system of claim 1, wherein said reaction temperature ranges between 230 F and 250 F.

3. The system of claim 1, further including a cooling unit operatively coupled to said pressure reaction chamber for cooling said pressure reaction chamber prior to unloading the infused oil final product from said pressure reaction chamber.

4. The system of claim 1, including a storage station operatively coupled to said pressure reaction chamber, wherein said at least one extraction vessel containing the infused oil final product and hermetically sealed is unloaded from said pressure reaction chamber and stored at said storage station for a predetermined storage duration.

5. The system of claim 4, including a final processing station operatively coupled to said storage station for compressing the unloaded infused oil final product, and fine filtering the compressed infused oil final product.

6. The system of claim 1, including a pre-extraction decarboxylating oven operatively coupled between said entrance station and said pressure reaction chamber for processing the hemp plant fine particles material in said pre-extraction decarboxylating oven at a temperature ranging from 200 F to 260 F for a time period of about one hour.

7. The system of claim 1, wherein said environmental equilibrium mechanism includes a lid attached to said at least one extraction vessel, and a valve installed in said lid, said valve establishing an environmental equilibrium between the interior of said pressure reaction chamber and the interior portion of said at least one extraction vessel.

8. The system of claim 1 wherein said hemp plant material is selected from the group of: a whole hemp plant, a freshly harvested hemp plant, or a dried hemp plant.

9. The system as recited in claim 1 including a second extraction vessel within said pressure reaction chamber in fluid communication with said first extraction vessel.

10. The system as recited in claim 9 wherein said first and second extraction vessel are joined each to the other by a connecting pipe to provide pressure and temperature equilibrium between said first and second extraction vessels.

11. The system as recited in claim 10 wherein said first and second extraction vessels form a manifold arrangement to provide a collective output from said reaction chamber.

12. The system as recited in claim 1 including at least one exit pipe in fluid communication with said at least one extraction vessel for removal of contents from said at least one extraction vessel for storage of said infused oil final product.

13. The system as recited in claim 1 including a post-decarboxylation oven fluidly in communication with said at least one extraction vessel for post-extraction of said infused oil final product.

14. The system as recited in claim 1 including at least a pair of extraction vessels within said pressure reaction chamber, each of said extraction vessels in fluid communication with the other.

15. The system as recited in claim 14 including a fluid conduit joining each of said extraction vessels to the other for permitting said fluid communication between said extraction vessels.

* * * * *